(12) United States Patent
Hayek

(10) Patent No.: US 8,689,791 B2
(45) Date of Patent: *Apr. 8, 2014

(54) RESPIRATORY APPARATUS

(76) Inventor: Shahar Hayek, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/217,903

(22) Filed: Aug. 25, 2011

(65) Prior Publication Data

US 2012/0192869 A1    Aug. 2, 2012

Related U.S. Application Data

(63) Continuation of application No. 10/568,489, filed as application No. PCT/GB2004/003525 on Aug. 16, 2004, now Pat. No. 8,020,556.

(30) Foreign Application Priority Data

Aug. 15, 2003  (GB) .................................. 0319255.6

(51) Int. Cl.
*A61M 11/00* (2006.01)
(52) U.S. Cl.
USPC ............. 128/205.25; 128/207.14; 128/204.18
(58) Field of Classification Search
USPC ............. 128/207.14–207.17, 205.25, 204.18
See application file for complete search history.

(56) References Cited

U.S. PATENT DOCUMENTS

| | | | |
|---|---|---|---|
| 3,014,480 A | 12/1961 | Gardner | |
| 3,362,404 A | 1/1968 | Beasley | |
| 3,216,413 A | 11/1969 | Mota | |
| 3,939,830 A | 2/1976 | de Costa | |
| 4,280,492 A * | 7/1981 | Latham | 128/207.15 |
| 4,646,732 A | 3/1987 | Chien | |
| 4,848,331 A * | 7/1989 | Northway-Meyer | 128/200.26 |
| 5,027,811 A * | 7/1991 | Tuxill | 128/207.14 |
| 5,303,701 A | 4/1994 | Heins et al. | |
| 5,372,130 A | 12/1994 | Stern et al. | |
| 5,404,874 A | 4/1995 | Meier | |
| 6,595,212 B1 | 7/2003 | Arnott | |

(Continued)

FOREIGN PATENT DOCUMENTS

| | | |
|---|---|---|
| CH | 685678 | 9/1995 |
| EP | 0164946 | 12/1985 |

(Continued)

OTHER PUBLICATIONS

Prosecution history for parent U.S. Appl. No. 10/568,489, filed Jun. 21, 2006 (downloaded Nov. 23, 2011), last document dated Aug. 31, 2011, 51 pp.

(Continued)

*Primary Examiner* — Steven Douglas
(74) *Attorney, Agent, or Firm* — Lathrop & Gage LLP

(57) ABSTRACT

Provided herein is a respiratory apparatus comprising a means for conducting breathable gasses directly to the trachea of a patient, via a tracheotomy or via a tube through the mouth to the trachea, and a means suitable for supplying the breathable gasses, under pressure, thereto and means for exhausting gases therefrom, characterised in that the pressuring means is so located as to impart pressure to said gasses immediately adjacent the site of the tracheotomy or the patient's mouth, thereby substantially reducing the length of the air supply hose to an endotracheal tube, so that problems associated with high pressures and large volumes of dead space can be alleviated.

25 Claims, 3 Drawing Sheets

(56) References Cited

U.S. PATENT DOCUMENTS

| | | |
|---|---|---|
| 8,020,556 B2 | 9/2011 | Hayek |
| 2003/0111074 A1 | 6/2003 | Alon et al. |
| 2003/0150458 A1 | 8/2003 | Arnott |
| 2007/0056588 A1 | 3/2007 | Hayek |

FOREIGN PATENT DOCUMENTS

| | | |
|---|---|---|
| EP | 0352938 | 7/1989 |
| FR | 2446115 | 8/1980 |
| JP | 10-323390 | 12/1998 |
| WO | 03/002205 | 1/2003 |

OTHER PUBLICATIONS

Search Report, dated Feb. 25, 2005, corresponding to International Application No. PCT/GB2004/003525 (filed Aug. 16, 2004), parent of the present application, 10 pp.

Search Report, dated Dec. 2, 2003, corresponding to Great Britain Application No. 0319255.6, related patent application, 1 pp.

Australian First Office Action, dated Mar. 5, 2010, in Australian Patent Application No. 2004264719, a related application, 2 pp.

Australian Second Office Action, dated Nov. 22, 2011, in Australian Patent Application No. 2004264719, a related application, 3 pp.

* cited by examiner

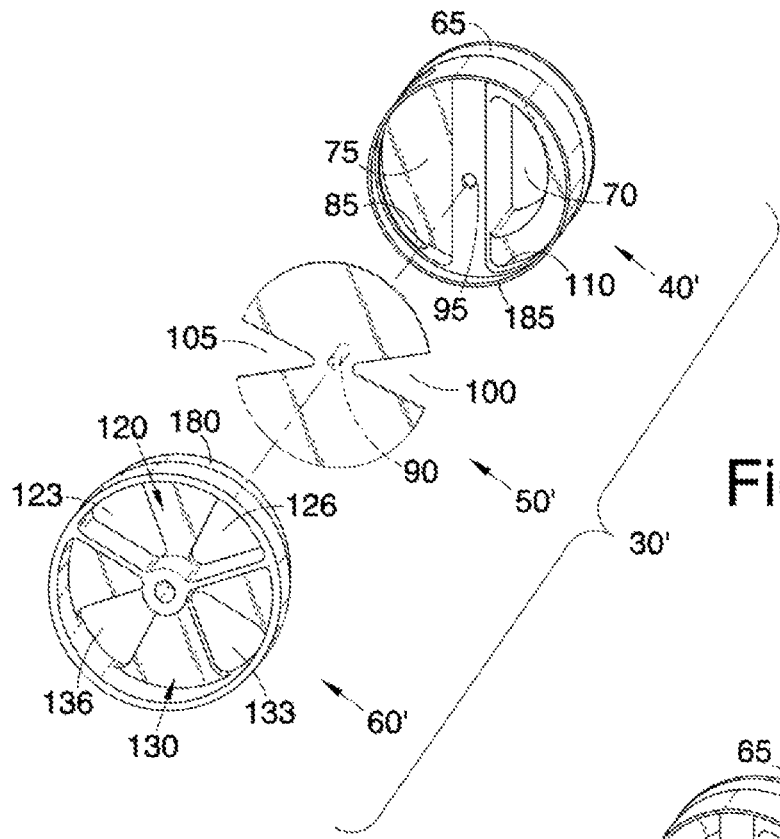
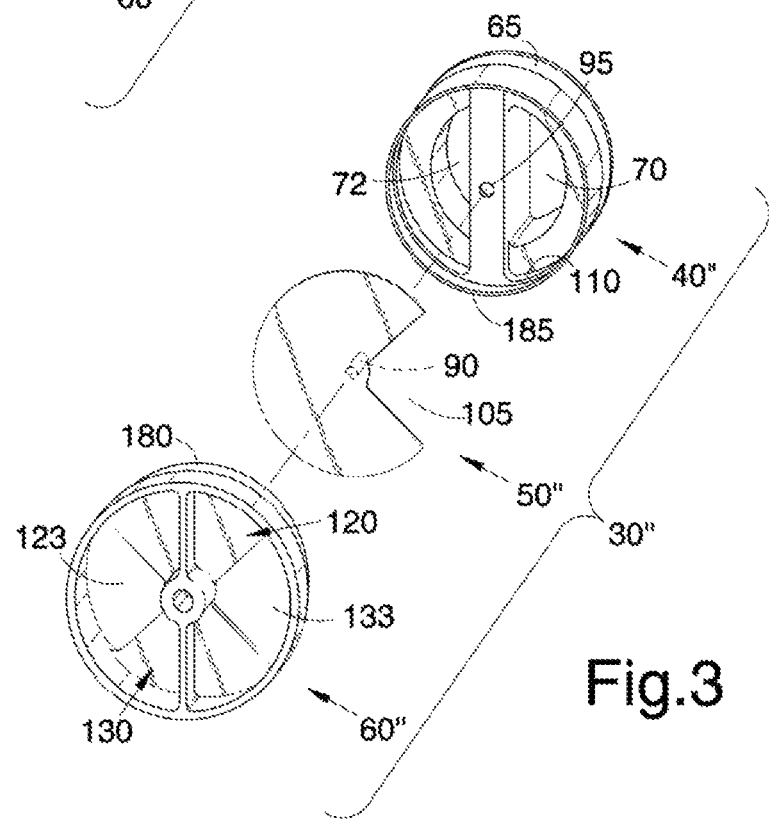

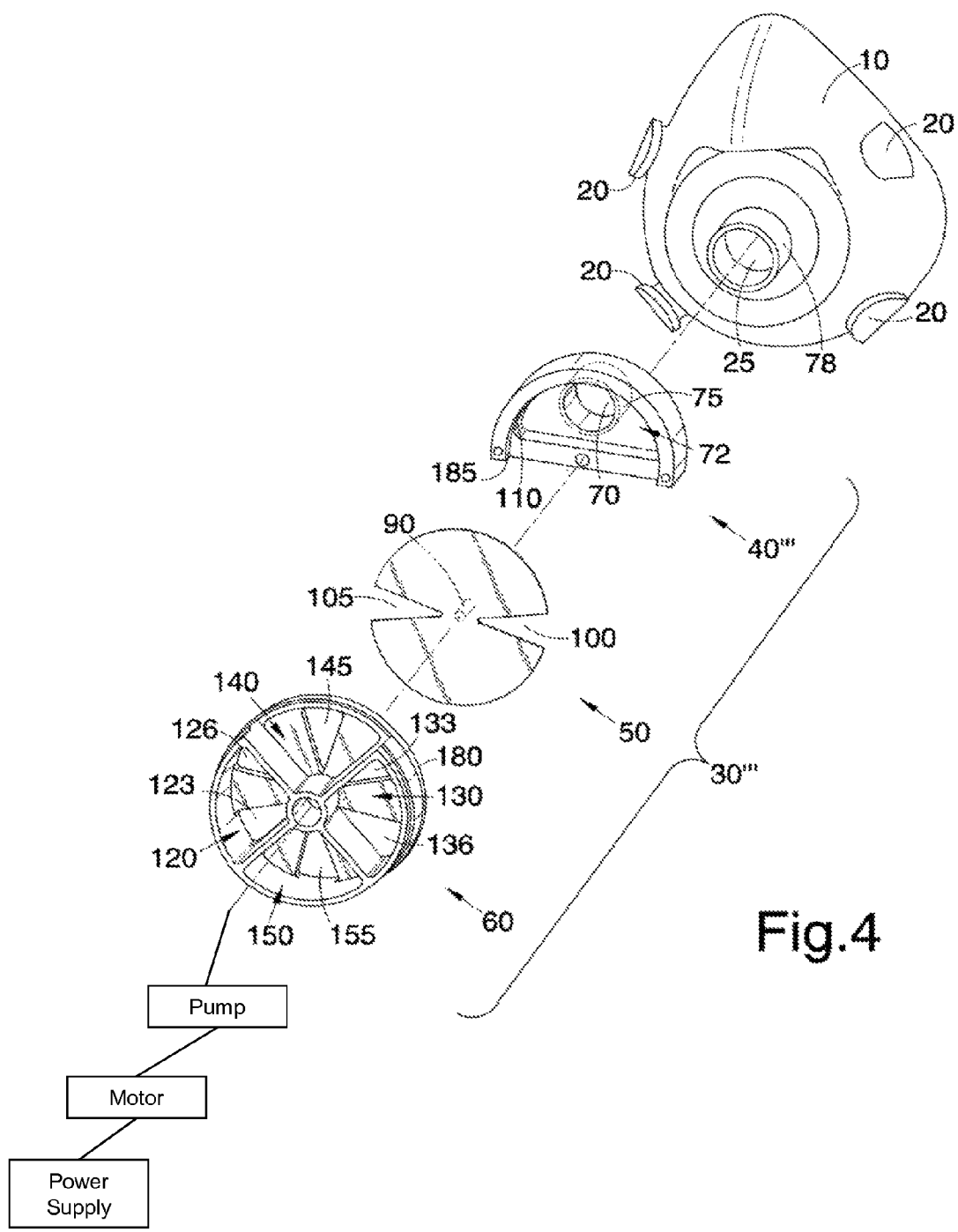

RESPIRATORY APPARATUS

REFERENCE TO RELATED APPLICATIONS

This application claims priority to U.S. application Ser. No. 10/568,489, filed Jun. 21, 2006 under 35 U.S.C. 371 as the national stage of PCT/GB2004/003525, filed Aug. 16, 2004, which application claims benefit of GB 0319255.6, filed Aug. 15, 2003, and which United States application issued on Sep. 20, 2011 as U.S. Pat. No. 8,020,556.

BACKGROUND

The present invention relates to respiratory, or ventilation, apparatus comprising a face mask and means for supplying pressurised air thereto, as well as to valves useful in such devices.

Non-invasive, mask-type ventilators, which include a face mask, pressurised air supply and valve, are known. These ventilators suffer from various disadvantages, primary amongst which is inflation of the abdomen via the oesophagus. As the stomach becomes inflated, this pushes up the diaphragm which, in turn, reduces lung volume and, concomitantly, tidal volume ($V_t$).

In addition, the ventilators of the prior art are not only cumbersome, but substantially restrict movement of the patient, as the pressurised air supply involves a length of tubing running from the mask to a fixed source of air or other suitable, breathable gas supply. The mask and tubing arrangement also tends to be heavy and somewhat inflexible, thereby putting further strain on the patient.

The substantial length of the tubing also tends to add somewhat substantially to the dead space. In this context, the dead space is that volume of air involved in the overall tidal flow which never comes into contact with gas exchange surfaces, in particular, the alveoli. When a patient is breathing normally, the dead space mainly comprises the trachea, nose and pharynx which, together, form about 150 ml of a total 600 ml tidal volume.

Using a mask of the prior art, the air supply tube may have a 10 mm internal radius and a length of 1800 mm, which provides an extra dead space, in addition to the 150 ml naturally occurring, of about 558 ml, thereby virtually doubling the tidal volume, as well as at least doubling the pressure required to effect satisfactory ventilation. It is such pressures which lead to problems with gas build up in the stomach.

One solution to the problem is to increase tidal flow and to create leaks in the mask to allow exhaust air, rich in carbon dioxide, to escape to help reduce the dead space problem. Another option is to provide a valve in the tubing to allow exhaled air to escape at an earlier stage. Both of these options still require substantial pressure to achieve satisfactory ventilation.

To achieve exhaust of $CO_2$ in current masks, continuous positive flow and, therefore, pressure is required, even during exhalation of the patient. The pressure required to achieve this flow is around 8 cm $H_2O$ or greater. This forms the basic expiratory pressure which the patient faces at exhalation and which needs to be overcome in order for the patient to exhale. This pressure increases the work of breathing and distends lung volume, potentially beyond the need of the patient, while at least the same amplitude (the difference between peak inspiratory and trough expiratory pressures) is required to achieve adequate tidal volume, so that 0-10 cm $H_2O$ for a normal patient becomes 8-18 cm $H_2O$ (or more) for a patient using a face mask. The effects may be even more deleterious, as tidal volume of 0-10 cm $H_2O$ is greater than 8-18 cm $H_2O$ due to the lung pressure-volume curve.

One type of mask ventilator providing positive pressure ventilation, and which is non-invasive, is disclosed at page 609 of "Respiratory Care Equipment", $2^{nd}$ edition, 1999. A valve therein relies on natural exhalation, so that it is activated by expiration to cut off or reduce the supply of positive pressure, thereby enabling the patient to breathe out. In this type of ventilator, only one phase of the respiratory cycle, the inspiratory phase, is assisted and therefore active. This has the disadvantage that it is not possible to increase the respiratory rate above 4-30 cycles per minute, as there is no option to do anything other than rely on the natural expiration of the patient. As passive recoil generally requires a minimum of one second, this means that such ventilators cannot work at more than 30 cpm. There is an exhaust valve in the power unit, so that dead space is still a problem, and there is a single pressure chamber through which air from the blower passes, either to the patient during inhalation, or through an exhaust, during exhalation in order to reduce or cut off supply.

Swiss Patent no. CH685678 discloses an inhaler comprising a base-shaped container in which pressurised oxygen is stored. French Patent Application No. FR2446115 discloses a resuscitator, which fits over the mouth of the patient to supply air from a bulb, further comprising a tongue depressor. Pressure, created by a hand-operated airbag or bulb, forces air into the mouth of the patient.

U.S. Pat. No. 3,216,413 discloses a hand-operated concentric bellows-type resuscitator apparatus for artificial respiration without a hose, wherein one bellows is situated within a second bellows, and there is an arrangement of valves to enable assisted inhalation and exhalation of air from the patient's lungs at the appropriate pressures.

U.S. Pat. No. 3,939,830 discloses a manually operated resuscitator or dechoker for removing an obstruction from the throat of a patient. In and out strokes of a piston are used to inflate and deflate the lungs of the patient.

US Patent Application no. 2003/0111074 discloses a positive pressure hood comprising a power operated blower which forces air through a filter in order to generate a positive pressure within the hood. A one-way purge valve exists for the exhaust of exhaled gases. The apparatus is only suitable for maintaining a clean air supply, for instance in a laboratory or other contaminated environment, inside the hood and, therefore, is not suitable for respirating a patient European Patent Application no. 0 352 938 discloses a powered respirator comprising a motor driven fan unit which draws air through an upstream filter unit, or alternatively, forces air through a downstream filter unit, for delivery to a face piece. The fan is triggered by a pressure sensor, which detects inhalation or exhalation by the patient leading to a corresponding assistance by the fan. Therefore, this device requires the patient to be breathing in the first place and cannot, therefore, be considered a respirator.

SUMMARY

The object of the device disclosed in European Patent Application No. 0 352 938 is to save battery life by only triggering the fan when inspiration is required. This is achieved by matching fan output to the inhalation of the user. Furthermore, the apparatus comprises significant dead space of its own, as can be seen in FIG. 1, with the associated problems this entails, as discussed above.

Surprisingly, it has now been found that, by substantially reducing the length of the air supply hose, problems associated with high pressures can be alleviated.

Thus, in a first aspect, there is provided respiratory apparatus comprising a ventilation mask and means for supplying breathable gasses, under pressure, thereto and means for exhausting gases therefrom, characterised in that the pressurising means is provided substantially at the inlet of the mask.

By supplying the pressurising effect at the inlet of the mask, rather than at a distance through a tube, the creation of a substantial amount of dead space is avoided, and substantially lower pressures and flow are effective to achieve ventilation, given that less $CO_2$ needs to be flushed out, as there is little or no tube. Indeed, it is now possible to use sufficiently low pressures that portable, battery operated devices can be employed and worn by patients, thereby allowing substantially unfettered movement, where the patient is capable.

In order to provide the required pressure at the mask interface, a suitable fan pump may be provided. The fan may be driven directly by a power supply and motor co-located therewith. Alternatively, the power supply, for example in the form of batteries, may be provided elsewhere, such as in a pocket. It is also feasible for the motor to be provided at a distance, and linked by a suitable gear link or train to the fan.

In general, it is preferred that a lightweight, motorised air pump be provided, mounted directly on the mask, with a remote power supply connected, for example, by suitable cables, or other means. Suitable pumps are centrifugal impeller blowers, of the type illustrated at the website of rietschle, principles/radial.asp, suitably miniaturised, or otherwise adapted, to provide a preferred maximum flow of 50 L/min. This contrasts with the 180 L/min used in the art, and reflects the benefits of the present invention, as well as enabling a portable power source to be used.

It is preferred that the maximum inspiratory pressure output be in the region of 25 cm H2O, with a range of 5-12 cm $H_2O$ being preferably employed, in use. Again, this compares extremely favourably with the standard 15-20 cm $H_2O$ and up to 30-35 cm $H_2O$ used in standard mask ventilators. The pressures used in the present invention are considerably more effective than those used in the art, as dead space and tidal volume problems are minimised, and there is much better response at lower pressures, as seen in pressure volume curve. It is preferred that the pumps used in the present invention have a voltage requirement of no more than 24V, preferably no more than 15V, with a range of 6-12V being preferred, although any pump or impeller capable of providing the requisite flow may be used.

The air supplied for breathing by the patient may simply be atmospheric air, in which case there is not generally any requirement for a supply, other than an atmospheric supply. However, where any other form of breathable gas is required or desired, then this may be supplied in any suitable fashion to the pump or, if only required in less than 100% quantities, independently of the pump.

The exhaust means may comprise a simple valve in the mask which is not generally activated by the pressure generated by the pump, alone, but is only activated by exhalation of the patient.

Whilst this embodiment provides many advantages over the prior art, it is generally preferred to enhance the respiratory apparatus of the invention by further incorporation of a valve to regulate air, or gas, pressure supplied to the mask.

It is also preferred to employ both the inlet and exhaust ports of the pump when providing ventilation in association with such a valve. Particularly suitable pumps for use in this connection are lightweight, centrifugal pumps, such as illustrated above, which draw air in at, or near, the rotational axis of the fan and generate an increased air pressure at the perimeter of the rotor, or impeller, which can be expressed via a suitable port. In an advantageous embodiment, both the inlet and the outlet ports of a centrifugal fan are provided in the same face of the pump. This has the advantage of facilitating interaction with the valve.

It is a particular advantage of this aspect of the present invention that it is possible to fully control the I/E Ratio (the inspiratory to expiratory time ratio), as there is no dependency on passive recoil of the lungs, so that both phases of the respiratory cycle may be fully controlled and active, allowing the I/E Ratio to be varied to practically any desired level.

Suitable valves of the present invention may comprise two body portions separated by a rotatable valve plate. A first body portion interacts with the ventilation mask, and may be secured thereto by any appropriate means, either fixedly or removably. Where the body portion is removable, attachment may be by any suitable means, such as interference fit, push fit or snap fit, for example.

The first body portion preferably defines a mask access chamber connecting both to the interior of the mask and the valve plate, and an exhaust chamber having an outlet to the atmosphere and connecting with the valve plate, but not the ventilation mask. Communication between the two chambers is generally prevented by the valve plate.

The valve plate locates over the first valve body and has openings to provide communication between the chambers of the first valve body and the second valve body portions. Movement of the plate, such as by rotation, serves to define how the chambers of each valve body portion communicate with the other. For ease, the openings in the valve plate are generally sectorial and identical in size, and it is preferred that the valve plate works in a back-forwards, or contra-rotatory, motion, in this case allowing complete control of the I/E ratio to be achieved through control of the time spent in the different sections of the valve. As such, it is also generally preferred that the valve section or, at least that part containing the valve plate, is circular, although it will be appreciated that the housing and walls surrounding the valve may be any appropriate configuration, as desired, and may have any appropriate configuration suitable to manual manipulation, for example.

It is preferred that the valve plate be mounted on a spindle or other actuatable means suitable to effect movement to locate the apertures in the plate in conjunction with the appropriate chambers in the valve body portions. The spindle may be actuatable by a second motor means, for example. This second motor is preferably controlled and may be responsive to the patient (in a triggered or synchronised mode) or external settings (in a controlled mode).

When responsive to the patient, exhalation may trigger the plate to move to allow or encourage exhalation. Similarly with inhalation, as both phases of the respiratory cycle may be fully and actively controlled. Suitable detector elements located in the mask can provide a signal to an effector associated with the motor.

Alternatively, the pump may be controlled independently of the patient's breathing, and set to a certain required pressure, for example. With the valves of the invention, the speed and number of cycles can be determined and this can readily exceed 1000/minute cpm or even higher.

The second valve body portion comprises at least two chambers, one of which is enclosed and corresponds to the pressurised air, or gas. The other chamber serves as a conduit for exhaust air. Both chambers are located to communicate with the chamber in the first body portion communicating with the mask, depending on the positioning of the valve plate. Where it is desired that the patient should simply exhale, and not be subject to any pressure, either positive or negative, then the exhaust chamber in the second valve body portion may be open to the atmosphere. This chamber, or a further chamber, may be connected to the inlet of the pump, in order to subject the patient to negative pressure to encourage exhalation, in which case it will be appreciated that the chamber will connect only with the inlet of the pump on the one hand and the connecting chamber of the first body portion on the other hand, when the valve plate is in the correct configuration.

In a preferred embodiment, a valve of the invention has three possible settings, providing the patient with positive pressure, negative pressure or simply atmospheric pressure. In this embodiment, the second body portion of the valve will comprise at least three chambers. A fourth, null chamber, or simple land, may be provided opposite the atmospheric chamber, for example. Where a null chamber is provided, this may be open, if desired.

It will be appreciated that, when the outlet of the pump is connected to the connecting chamber in the first body portion of the valve, then the inlet of the pump will be connected to the chamber in the first body portion of the valve which connects and, therefore, is exhausted to the atmosphere. Likewise, when the inlet is connected to the connecting chamber, then the outlet will be connected and exhausted to the atmosphere.

The above pump embodiments are particularly preferred, and form a separate aspect of the invention and, in particular, for use with respiratory apparatus of the present invention, or any other respiratory apparatus.

The ventilation mask is not critical to the present invention. Conventional masks may be used or adapted, and it is generally preferred that they provide a substantially gas-tight linkage with the airways of the patient.

The present invention may also be applied to an apparatus where the mask portion is replaced by an endotracheal tube or means for connecting to such a tube.

Thus, in a further aspect, the present invention also provides a respiratory apparatus comprising a means for conducting breathable gasses directly to the trachea, via a tracheotomy or via a tube through the mouth to the trachea, and a means suitable for supplying the breathable gasses, under pressure, thereto and means for exhausting gases therefrom, characterised in that the pressuring means is provided substantially at the site of the tracheotomy or the patient's mouth.

The means for conducting breathable gasses directly to the trachea is preferably an endotracheal tube with, optionally, a standard connection from the endotracheal tube to the means suitable for supplying the breathable gasses.

Alternatively, the means for conducting breathable gasses directly to the trachea is preferably a connecting means for linking the apparatus in a substantially air-tight manner to an existing endotracheal tube.

The endotracheal tube may be connected to the rest of the device through the patient's mouth and tracheal opening, or, more preferably, through a hole or incision in the patient's throat, for instance a tracheotomy. In this instance, the pressuring means is provided substantially at the inlet of the tracheotomy.

Thus, this aspect of the present invention is preferably suitable for use in conventional invasive positive pressure ventilation (PPV), for instance on a patient with a tracheotomy. Thus, the apparatus is, preferably, an invasive respirator.

The apparatus may also be suitably adapted as described in the present application with respect to the mask aspect of the invention. In particular, the apparatus may comprise a valve, preferably as described herein.

The apparatus can, preferably, operate as either a positive pressure ventilator or a high frequency oscillator.

There are several advantages to using this aspect of the invention, for instance as an invasive respirator. A direct connection can be made from the apparatus to the endotracheal tube, thus minimising the tubing required. The advantage this gives is again a reduction in dead space during ventilation (although there is already less dead space in PPV than in mask ventilators) and, therefore, lower pressures are required to adequately ventilate patients. Again, this helps avoid the negative side effects of high pressures. Furthermore, as the apparatus can be directly connected to the trachea, this can result in a significant decrease in the dead space associated with the patient's trachea and mouth, for instance as much as 50%.

The endotracheal tube may also form part of the mask according to the present invention, such that the respiratory apparatus comprises both a mask and an endotracheal tube.

The apparatus is easy to clean and sterilize, as it has few parts and little or not rubbing, thus reducing the risk of infection for the patient. Furthermore, the apparatus is small, lightweight and this, with the option of being battery operated, allows the invention to be used as a mobile respirator that also takes up far less space when used in the intensive care. Monitoring can be done as in conventional ventilators by sending the information in a wireless manner, such as Bluetooth or infrared, for instance.

Most mobile transport ventilators are either fairly large battery operated devices requiring substantial amounts of battery power or most commonly (due to this reason) smaller pneumatic devices that require compressed air for them to work. (See chapter 17, Branson et al., "Transport Ventilators," p527-565, Respiratory Care Equipment).

Pressures suitable for generation by the apparatus of the present invention are generally low by comparison with the prior art, and suitable pressures have been found, for the mask, to be typically be 5-12 cm $H_2O$ above ambient pressure and, as a maximum, 25 cm $H_2O$ during the inspiratory phase and from a maximum of −5 cm $H_2O$, to below, at or above ambient pressure during the expiratory phase.

In the case of the endotracheal apparatus the pressures generated can be higher and are typically from a maximum of 40 cm $H_2O$ during the inspiratory phase and from a maximum of −15 cm $H_2O$, to below, at or above ambient pressure during the expiratory phase.

These pressures are for guidelines only, and it will be appreciated that higher pressures, as well as lower pressures, may be employed, but these require greater input of power, and may be associated with the problems of the prior art.

The present invention further provides a method of ventilating a patient, comprising equipping the patient with the apparatus, particularly the mask, as defined above, and activating the pump.

Preferably, the apparatus comprises a supply of oxygen or breathable gasses, for instance in a pressurised vessel or tank, or via a connection to a source of said gasses. Preferably, an oxygen supplement is fed through a connection to the apparatus, preferably to the valve, in order to increase $FiO_2$ (Fraction of Inspired Oxygen) to above room air level.

Any condition treatable by conventional ventilation apparatus or masks may be treated in accordance with the present invention, and may cover patients with sleep apnoea and lung diseases to those on life support, as may be directed by a skilled physician. Therefore, also provided is a method of ventilating a patient in need thereof, comprising the use of an apparatus according to the present invention.

Preferably, the apparatus is a respirator or ventilator. It is also preferred that the apparatus according to present invention controls the breathing rate of the patient, rather the apparatus being triggered by the breathing of the patient. Preferably, therefore, according to this embodiment of the present invention, inspiration and expiration are not triggered by the patient of his or her breathing, but are controlled by a suitable control device, such as life support machine, for instance. Accordingly, the present invention may be used on a patient that is not breathing on his or her own.

In a further embodiment of the present invention, the apparatus may also comprise a filter for removing contaminants, for instance, from the inspired and/or expired air.

Preferably, the apparatus comprises means for reversibly securing the apparatus to the face or neck of the patient, as appropriate, thereby allowing the apparatus to be held in place and/or used in a substantially hands-free manner, without the patient having to hold it in place. For instance, where the apparatus is a mask, it is preferred that the means for reversibly securing the apparatus comprises at least one or a plurality of straps or ties, suitable for the purpose, that may be passed around the patient's head. The straps or ties are preferably elastic.

Where the apparatus comprises an endotracheal tube, it is preferred that the straps or ties are suitable for passage around the patient's neck, for instance. The apparatus may also comprise a series of flanges which may be used to secure the apparatus to the patient by means of bandages.

Preferably, the additional dead space added by the apparatus to that naturally occurring in the patient, is kept to an absolute minimum, preferably 200 ml or less, more preferably 100 ml or less, preferably 50 ml or less, preferably 20 ml or less, preferably 25-50 ml, preferably 10-20 ml, preferably 10-15 ml, preferably 5-10 ml more preferably 10 ml and most preferably 5 ml or less.

The apparatus is also preferably biphasic such that it not only forces air into the patient's lungs, but also actively expels the air from the lungs, rather than simply allowing the lungs to deflate naturally of their own accord, as is the case in many of the prior art devices. Both phases may be triggered by the patients breathing, or may be under the control of the apparatus, under the control of an onboard processor, or under the control of a further control means, such as a life-support machine, for instance. This has the advantage of providing the user or doctor with a greater degree of control with respect to the inspiration/expiration rate.

BRIEF DESCRIPTION OF THE DRAWINGS

The invention will now be further illustrated with reference to the accompanying drawings, in which:

FIG. 2 illustrates a valve of the present invention having two pressure settings;

FIG. 3 illustrates a valve for use with the present invention; and

FIG. 4 illustrates an alternative embodiment of the valve of FIG. 1.

DETAILED DESCRIPTION

Figure 1:
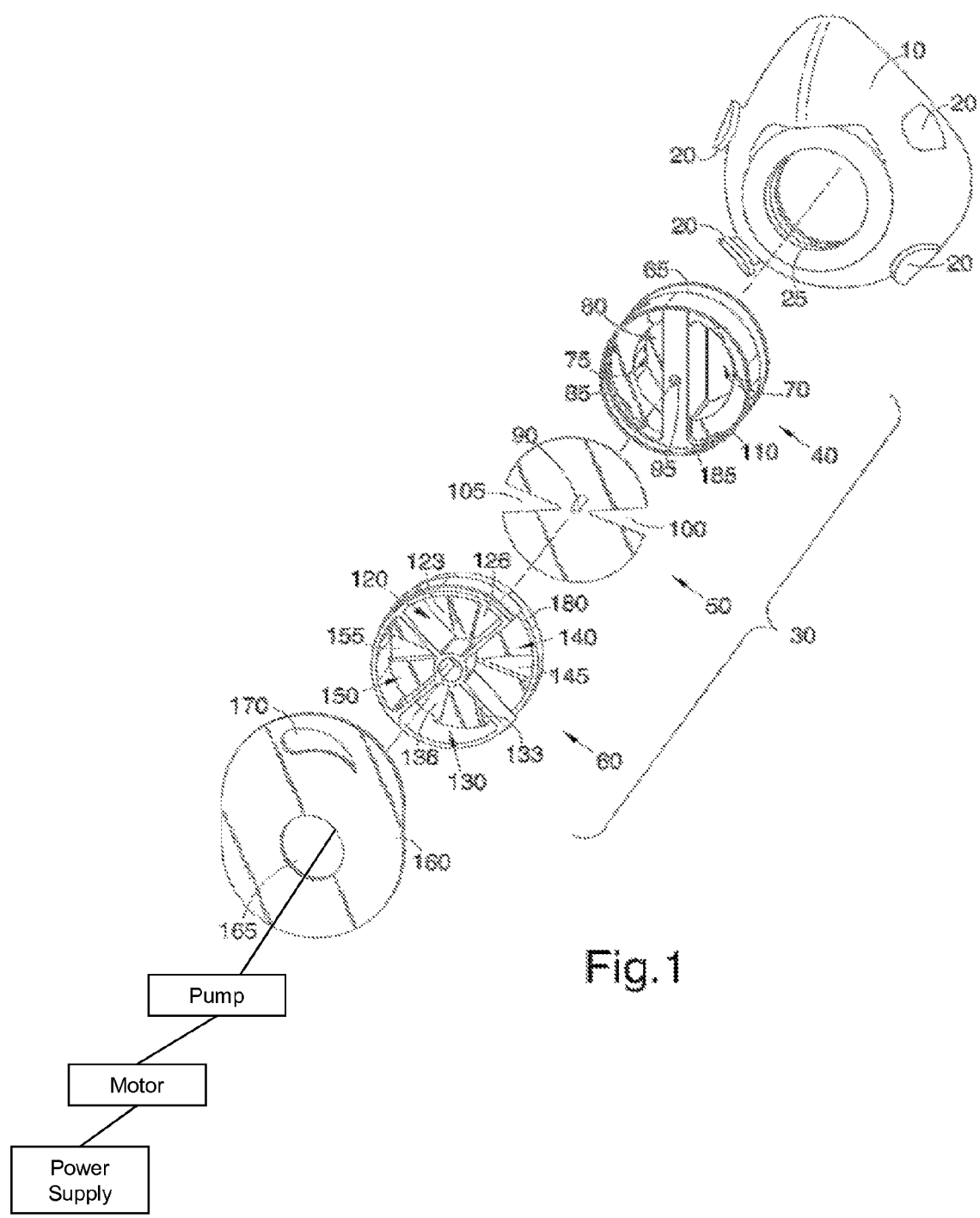
FIG. 1 illustrates a mask and valve of the present invention where the valve has three pressure settings.

In FIG. 1, there is shown face mask (10) having processes (20) for the attachment of straps, or the like, to secure the mask (10) over the mouth and nose of the patient (not shown).

Valve (30) is shown in three sections (40, 50, 60) and is locatable in aperture (25) of mask (10) via flange (65) of first body portion (40). Connecting chamber (70) provides an unobstructed passageway between the inside of mask (10) and valve plate (50). Chamber (75) is sealed by land (80), and does not provide gaseous communication with the inside of mask (10). Exhaust slot (85) provides communication with the external atmosphere.

Valve plate (50) is provided with spindle (90), which locates in corresponding recess (95) in first valve body portion (40). Spindle (90) is suitably equipped with external drive means (not shown) to effect rotation.

Apertures (100, 105) control communication between first valve body portion (40) and second valve body portion (60). The periphery of the valve plate (50) locates on internal flange (110) in valve body portion (40), thereby providing a gas-tight seal, or substantially gas-tight seal. It will be appreciated that with the general volume of air flow, it is not necessarily important that the seal be especially gas-tight, provided that any gas getting past the seal does not substantially interfere with the desired ventilation effect.

Second valve body portion (60) is equipped with four chambers (120, 130, 140, 150) equipped with slots (123, 126, 133, 136, 145, 155). Impeller end plate (160) is shown, with negative pressure port or inlet (165) and positive pressure port, or outlet (170). The rest of the impeller is not shown. Positive port (170) corresponds with chamber (120) of second valve body portion (60), while negative port (165) corresponds with chamber (130). When aperture (100) is located over aperture (133), then aperture (105) will be located over aperture (123). In this configuration, negative port (165) communicates via aperture (133) and aperture (100) with communicating chamber (70) to reduce the pressure in mask (10). At the same time, positive pressure port (170) acts via apertures (123, 105) to exhaust via slot (85) in dead end chamber (75).

Rotating the valve plate (50) to engage aperture (100) with aperture (136) places aperture (105) in conjunction with aperture (126), so that the reverse effect is achieved. Namely, negative port (165) communicates via apertures (136) and (100) with null chamber (75) to draw in air through slot (85) while positive pressure port (170) communicates via apertures (126) and (105) with communicating chamber (70) to raise the pressure in the mask (10). It will be appreciated that the same effect will be achieved if aperture (105) corresponds to aperture (136) rather than aperture (126), and that the one configuration of the two possible is described for purposes of simplicity. Similar considerations apply to any other configuration where a plurality of equivalent possibilities exists.

In a third configuration, apertures (105) and (100) interact with apertures (145) and (155), respectively. In this configuration, as with all other configurations of this embodiment, neither chamber (150) nor open chamber (140) corresponds to any port on the impeller. Thus, in this configuration, the effect is to provide a direct atmospheric link to the mask via connecting chamber (70) and apertures (100) and (145), the lack of wall in chamber (140) providing immediate access to the atmosphere.

In FIG. 2, valve (30') is shown, consisting of first valve body portion (40'), valve plate (50') and second valve body portion (60'). In this embodiment, the numerals have the same meanings as in FIG. 1.

An alternative version of the first valve body portion (40') is shown, in which the chamber (75) is not hollowed in any fashion, thereby simply providing an aperture (85) communicating with the atmosphere, in the chamber.

In second valve body portion (60'), chambers (140) and (150) are not present, so that only positive pressure chamber (120) and negative pressure chamber (130) are provided. In this configuration, negative pressure is provided to the ventilation mask when aperture (100) corresponds with aperture (133) and aperture (105) corresponds with aperture (123). Positive pressure is provided when aperture (100) corresponds with aperture (126) and aperture (105) of the valve plate (50') corresponds with aperture (136).

In FIG. 3 valve (30") is for use with a blower where only the positive pressure outlet engages with chamber (120) of valve body portion (60"). Chamber (130) is open to the atmosphere. There is no slot (85) in valve body portion (40"). Instead, chamber (72) connects directly to opening (123) in valve body portion (60") when opening (105) in valve face plate (50") is appropriately located.

When opening (105) corresponds with opening (133), then positive pressure is fed into the mask via chamber (70), while chamber (72) is closed by valve face plate (50").

Valve face plate (50") may also occupy a central position where slot (105) corresponds to neither opening (123) nor opening (133), so that air may neither pass in nor out of the mask in this configuration. This may be appropriate between inhalation and exhalation, for example.

As with FIGS. 1 and 2, recessed portion (180) locates within and abuts against lip (185) on valve body section (40").

FIG. 4 depicts a valve embodiment similar to that of FIG. 1, and functions in a similar manner. In this embodiment, valve body portion (40''') is lacking land portion (72) such that, when any of openings (136), (155) and (123) is exposed by either of openings (100) and (105), then direct contact with the ambient atmosphere is made.

Chamber (70) in body portion (40''') takes the form of a lumen in male member (75) which docks with female member (78) in the mask (10). Openings (126), (145) and (133) communicate with lumen (70) when exposed thereto by either of openings (100) and (105) via chamber (72) recessed beneath flange (110), providing positive, negative or atmospheric pressure, as desired.

It will be appreciated that variations are possible in the embodiments of the above Figures and that it is possible to vary the amount of pressure in the mask by varying the degree to which any particular aperture is open. For example, it may be desirable to continue to provide a lesser positive pressure during exhalation rather than atmospheric or negative pressure. Where desired, this may be effected either by lowering pressure in the blower, or preferably by controlling pressure through the I/E Ratio, thereby maintaining an overall positive pressure in the mask, even where the disc is allowing atmospheric or negative pressure into the mask. Although it is possible to vary the speed of the impeller, it is generally preferred to keep this at a constant rate, except when the ventilation device is switched off, in order to conserve energy and provide the most rapid possible reaction time.

The invention claimed is:

1. A respiratory apparatus comprising a means for conducting breathable gasses directly to the trachea of a patient, via a tracheotomy or via a tube through the mouth to the trachea, and a means suitable for supplying the breathable gasses, under pressure, thereto and means for exhausting gases therefrom, characterised in that the pressuring means is so located as to impart pressure to said gasses immediately adjacent the site of the tracheotomy or the patient's mouth.

2. The respiratory apparatus according to claim 1, wherein a motor for the pressuring means is co-located therewith.

3. The respiratory apparatus according to claim 1, further comprising a power supply which is portable.

4. The respiratory apparatus according to claim 3, where the power supply is in the form of batteries.

5. The respiratory apparatus according to claim 1 wherein the pressuring means is a centrifugal impeller blower.

6. The respiratory apparatus according to claim 1, wherein both the inlet and exhaust ports of the pressuring means are communicable with an endotracheal tube or means for connecting to such a tube, in use.

7. The respiratory apparatus according to claim 5, wherein the inlet and the outlet ports of the centrifugal impeller blower are provided in the same face of the pressuring means.

8. The respiratory apparatus according to claim 1, further incorporating a valve to regulate air, or gas, pressure in the apparatus.

9. The respiratory apparatus according to claim 8, wherein the valve regulates air, or gas, pressure in an endotracheal tube.

10. The respiratory apparatus according to claim 9, wherein the valve comprises two body portions separated by a rotatable valve plate,
   the first body portion interacting with the endotracheal tube and defining an endotracheal tube access chamber connecting both to the interior of the endotracheal tube and the valve plate, and an exhaust chamber having an outlet to the atmosphere and connecting with the valve plate, but not the endotracheal tube;
   the valve plate locating over the first valve body portion and having openings to provide communication between chambers of the first valve body portion and the second valve body portion;
   the second valve body portion comprising at least two chambers, one of which is enclosed and corresponds to the pressurised air, or gas, and the other serving as a conduit for exhaust air, both chambers being located so as to communicate with the chamber in the first body portion communicating with the endotracheal tube, as determined by positioning of the valve plate.

11. The respiratory apparatus according to claim 10, wherein the valve has three possible settings to provide the patient with positive pressure, negative pressure or atmospheric pressure, and wherein the second body portion of the valve comprises at least three chambers, an optional null chamber, or land, being provided opposite the atmospheric chamber, and wherein the atmospheric chamber exhausts directly to the atmosphere.

12. The respiratory apparatus according to claim 8, wherein the inspiratory to expiratory time ratio is under the control of the apparatus.

13. The respiratory apparatus according to claim 8, wherein the apparatus has the ability to operate at high frequency, up to 1000/minute cpm, or greater.

14. The respiratory apparatus according to claim 1 which is a respirator or ventilator.

15. The respiratory apparatus according to claim 1, wherein the apparatus controls the breathing rate of the patient.

16. The respiratory apparatus according to claim 1, wherein the means for conducting breathable gasses directly to the trachea is selected from the group consisting of: an endotracheal tube with, optionally, a standard connection from the endotracheal tube to the means suitable for supplying the breathable gasses; and a connecting means for linking the apparatus in a substantially air-tight manner to an existing endotracheal tube.

17. The respiratory apparatus according to claim 1, wherein the endotracheal tube is connected to the rest of the device through a tracheotomy.

18. The respiratory apparatus according to claim 1, wherein apparatus is an invasive respirator.

19. The respiratory apparatus according to claim 1, wherein the pressure generated by the apparatus is from a maximum of 40 cm H2O during the inspiratory phase and from a maximum of −15 cm H2O, to below, at or above ambient pressure during the expiratory phase.

20. The respiratory apparatus according to claim 1, wherein the apparatus comprises a means for reversibly securing the apparatus to the face or neck of the patient.

21. The respiratory apparatus according to claim 1, wherein the additional dead space added by the apparatus is selected from the group consisting of: 25-50 ml, or less; and 5-10 ml, or less.

22. The respiratory apparatus according to claim 1, wherein the apparatus is biphasic.

23. A method of ventilating a patient in need thereof, comprising the use of an apparatus according to claim 1.

24. A valve comprising two body portions separated by a rotatable valve plate, the first body portion adapted to interact with a ventilating interface and defining a chamber connecting both to the interior of the ventilating interface and the valve plate, and an exhaust chamber having an outlet to the atmosphere and connecting with the valve plate, but not the ventilating interface;

the valve plate locating over the first valve body portion and having openings to provide communication between chambers of the first valve body portion and the second valve body portion;

the second valve body portion comprising at least two chambers, one of which is enclosed and corresponds to the pressurised air, or gas, and the other serving as a conduit for exhaust air, both chambers being located so as to communicate with the chamber in the first body portion communicating with the ventilating interface, as determined by positioning of the valve plate.

25. The valve according to claim 24, wherein the valve plate is mounted on a spindle actuatable by a second motor.

* * * * *